United States Patent [19]

Chang et al.

[11] Patent Number: 4,465,635
[45] Date of Patent: Aug. 14, 1984

[54] MANUFACTURE OF PALLADOUS CARBOXYLATES

[75] Inventors: Biau-Hung Chang; Anil B. Goel, both of Worthington, Ohio

[73] Assignee: Ashland Oil, Inc., Ashland, Ky.

[21] Appl. No.: 443,349

[22] Filed: Nov. 22, 1982

[51] Int. Cl.³ .............................................. C07F 15/00
[52] U.S. Cl. .................. 260/414; 260/429 R
[58] Field of Search ........................... 260/429 R, 414

[56] References Cited

U.S. PATENT DOCUMENTS 3,318,891 5/1967 Hausman et al. ............ 260/429 R X
3,437,431 4/1969 Platz ........................... 260/429 R X
3,484,235 12/1969 Goss et al. ................... 260/429 R X

OTHER PUBLICATIONS

Stephenson et al., Jour. Chem. Soc., pp. 3632-3640, (1965).

JACS 93, 1497, 1499, (1971).

Primary Examiner—Helen M. S. Sneed
Attorney, Agent, or Firm—John F. Jones

[57] ABSTRACT

A novel method for preparing soluble

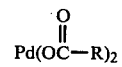

by reaction of palladium metal with a carboxylic acid of the formula RCOOH wherein R is a hydrocarbon or halogenated hydrocarbon group having from 1 to 10 carbon atoms in the presence of a member selected from the group consisting of A. $HNO_3$ plus NO, B. $HNO_2$, C. nitric oxide plus oxygen, D. nitric oxide plus nitrogen dioxide, E. nitrogen dioxide, and F. nitrosyl acetate, is described.

10 Claims, No Drawings

MANUFACTURE OF PALLADOUS CARBOXYLATES

This invention relates to the manufacture of the palladous salts of carboxylic acids and more particularly pertains to a novel method for the production of

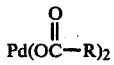

$$Pd(OC-R)_2$$

wherein R is a hydrocarbon group or halogenated hydrocarbon group having from 1 to 10 carbon atoms.

Palladium (II) salts of carboxylic acid such as palladium (II) acetate have been widely used as catalysts for both hydrogenation and oxidation reactions as is well known in the art. More recently there has been a need for a soluble form of palladium for use in the catalytic liquid phase oxidation of hydrocarbons and it is essential that such palladium catalysts be of high purity and essentially free of polymer, and certain negative ions such as chloride ions in certain of the palladium catalyzed reactions.

Crystalline palladium diacetate has previously been prepared by a four step process involving (1) forming hydrous palladium oxide (HPO), (2) nearly drying the HPO, (3) treating the partially dried HPO with acetic acid, and (4) separating the palladium diacetate from the acetic acid medium in the form of crystals which are described as yellow or yellow-tan needle-like crystals in U.S. Pat. No. 3,318,891 to Hausman et al. The Hausman et al patent stresses that polymeric HPO formation must be avoided in their process by observing certain precautions regarding water content and reaction temperature.

The preparation of diacetato palladium from palladium metal, acetic acid and oxygen pressure (80 atmospheres) or from palladium metal, acetic acid and perchloric acid gave incomplete reaction and sometimes leads to the formation of the pink, insoluble acetate which could not be purified by crystallization. See *ACS, DIV. PETROL, CHEM., PREPR.* 14, B23 (1969).

Another prior art method for the preparation of palladium diacetates is the reaction of palladium metal with acetic acid in the presence of $HNO_3$ as described in *Journal of the Chemical Society*, 3632 (1965). In a recent Japanese patent No. 126463 a used vapor phase palladium catalyst in conjunction with alkali metal salts has been reactivated by treating it with $HNO_3$.

In the prior art methods for preparation of palladium diacetate by the oxidation of palladium metal with $HNO_3$ it is difficult if not impossible to eliminate the presence of oxo-anions of nitrogen in the product and these impurities are known to alter the course of oxidation reactions. Many of the prior art methods result in the formation of some pink, insoluble palladium acetate which has been found to be a catalytically inactive form of palladium. The use of oxygen under pressure to form palladium acetate in acetic acid can cause combustion of the excess acetic acid present which creates a risk of explosions, particularly in large scale preparations.

As stated earlier, palladium acetate has been widely used as catalyst or as a catalyst component in various homogeneously catalyzed organic reactions. We have observed from time to time that "palladium diacetate" obtained by us from different sources existed in various forms and that the catalytic activity of these various forms varied widely. This unpredictability of the activity of "palladium diacetate" prompted a careful investigation on our part which resulted in the discovery of a novel process for the manufacture of a uniformly consistent catalytically active form of palladium diacetate and equivalent palladium dicarboxylates.

The most common method for the preparation of palladium diacetate (trimeric form) involves the reaction of palladium metal with acetic acid in the presence of $HNO_3$, perchloric acid, or $O_2$. We have found that these prior art methods usually yield some pink-colored, insoluble palladium acetate which has been found to have little or no catalytic action particularly in homogeneous oxidation reactions. This pinkish, insoluble form of palladium acetate which is insoluble in most organic solvents including benzene, toluene, other hydrocarbons, carboxylic acids, etc. is probably a polymeric form of palladium acetate as opposed to the soluble form (trimeric form) of palladium diacetate. Infrared analysis shows a strong band at about 1600 cm$^{-1}$ for the trimeric form of palladium diacetate whereas no band has been found in the 1500-1800 cm$^{-1}$ region for the pink polymeric palladium acetate form.

Palladium diacetate prepared from palladium metal in acetic acid with $HNO_3$ oxidant often contain trace amounts of oxoanions of nitrogen [*J.C.S. Dalton Trans.* 183 (1977)]. These impurities are already known to alter the course of the oxidation of olefins [*JACS*, 93, 1497 (1971)]; *JACS*, 93, 1499 (1971)].

We have discovered a single step method for the preparation of organic solvent soluble (trimeric) palladium diacetate which is free of contaminants which are known to interfere with its catalytic activity which involves the reaction of palladium metal with a carboxylic acid having the formula RCOOH wherein R is a hydrocarbon or halogenated hydrocarbon group having from 1 to 10 carbon atoms, such as acetic acid, in the presence of a member selected from the group consisting of A. less than 0.67 equivalent of $HNO_3$ per equivalent of palladium under an atmosphere of NO, B. with $HNO_2$, C. with NO and $O_2$, D. with NO and $NO_2$, E. with $NO_2$, and F. with nitrosyl acetate. The reaction is carried out at a temperature in the range of from 50° to 160° C. and preferably from 60° C. to 140° C. for from two minutes to four hours or longer. The resulting orange-red solution is then flushed with an inert gas such as nitrogen, argon, etc. to remove traces of the oxides of nitrogen and crystals of the desired soluble (trimeric) form of palladium diacetate are obtained from the concentrated solution.

The method of this invention can be used for the preparation of palladium salts of carboxylic acids having the formula RCOOH wherein R is a hydrocarbon group or a halogenated hydrocarbon group having from 1 to 10 carbon atoms such as acetic acid, trifluoro acetic acid, trichloro acetic acid, monochloro acetic acid, propionic acid, the butyric acids, the pentanoic acids, the hexanoic acids, the heptantanoic acids, the octanoic acids, the nonanoic acids, the decanoic acids, benzoic acid, cyclohexane carboxylic acid, etc. This is readily accomplished by substitution of the desired carboxylic acid for the acetic acid used in the illustrative process described above.

The process of this invention is further demonstrated in the following illustrative examples.

EXAMPLE 1

This example illustrates the preparation of the soluble, active (trimeric) form of palladium diacetate using palladium metal, acetic acid, $HNO_3$ and NO in accordance with this invention. Pd sponge (0.34 g.), 17.8 ml. of glacial acetic acid and 0.13 ml. of nitric acid were placed in a 100 ml. flask equipped with a condenser. The resulting mixture was heated at 90° to 98° C. under an atmosphere of NO for two hours. The resulting orange-red solution was filtered and concentrated to yield orange-red crystals of palladium diacetate in 99% yield. This crystalline palladium diacetate was found to be soluble in benzene, toluene and other hydrocarbons. Infrared analysis of these crystals showed a sharp band at 1600 and 1430 $cm^{-1}$.

EXAMPLE 2

This comparative example illustrates the prior art $HNO_3$ method which yields insoluble (polymeric) palladium diacetate which is relatively inactive as a catalyst. The apparatus described in example 1 was used. Palladium sponge (2 g.) was first allowed to react with 2.5 ml. of nitric acid at about 50° C. for ½ hour to produce a red colored solution. Next 70 ml. of acetic acid was added to the red solution and the resulting mixture was heated to reflux for 2 hours during which brown fumes evolved and an insoluble solid formed. The insoluble solid was removed by filtration and was dried under reduced pressure. The resulting pinkish-beige solid (90% yield) was found to be insoluble in benzene, toluene and other hydrocarbons and showed no bands in the 1500-1800 $cm^{-1}$ region when examined by infrared analysis. This solid material which is believed to be polymeric decomposes at about 232° C.

EXAMPLE 3

The palladium acetate solids described in examples 1 and 2 above were tested in the oxidation of toluene to the benzyl ester of dodecanedioic acid by a catalytic combination of 1.35 g. of the palladium acetate with 2.1 g. of lead acetate in an excess of dodecandioic acid at a temperature in the range of from 160° C. to 170° C. In the case in which the palladium acetate of example 1 was used, a high conversion (greater than 50%) of the toluene to benzyl ester was observed with a turnover number (moles of product per mole of palladium) of about 20 whereas a very low conversion (less than 5%) with a turnaround number of only about 2 was observed in the case in which the palladium acetate of example 2 was used in the catalyst.

EXAMPLE 4

Palladium diacetate was prepared from palladium sponge, acetic acid and $HNO_2$ by adding 0.295 g. of palladium sponge and 45 ml. of glacial acetic acid in the apparatus described in example 1. The resulting mixture was stirred at ambient temperature for about 2 hours with an occasional addition of gaseous $HNO_2$ to the mixture. The mixture was stirred overnight at ambient temperature and was then heated to 115° C. for one hour while being purged with argon. The resulting brown-red solution was filtered and the filtrate was concentrated to yield orange-red crystals of trimeric, hydrocarbon-soluble palladium diacetate in 96% yield.

EXAMPLE 5

The procedure of example 1 was followed by adding 0.3 g. of palladium sponge to the 100 ml. flask containing 40 ml. of $CF_3COOH$. To this was added 0.16 g. of $HNO_3$, the reaction mixture was heated to 70° C. and NO was bubbled into the reaction mixture for an hour under these conditions. At the end of this time the reaction mixture was flushed with argon which was bubbled through it for 2 hours at 70° C. The resulting mixture yielded a pink-brown solid which was removed by filtration and dried under reduced pressure (98% yield) and was found by infrared analysis to have bands at about 1576 and 1458 $cm^{-1}$.

EXAMPLE 6

The procedure of example 1 was followed except that the reaction mixture was made up of 0.32 g. of palladium sponge, 35 ml. of glacial acetic acid and 3 drops of water. The reaction temperature was from 100° to 110° C. and NO was bubbled slowly through the mixture under these conditions over a 40 minute period. During this time the reaction mixture was periodically flushed with air ($O_2$ source) so that a total of 200 ml. of air was used in this way during the course of the reaction. At the end of the 40 minute reaction time the reaction mixture was held at 108°-110° C. for an hour and argon gas was bubbled through the mixture during this time. The reaction mixture was then cooled to ambient temperature, the solution was concentrated and trimeric palladium diacetate precipitated out and was collected by filtration in nearly quantitative yield. The trimeric palladium diacetate crystals were orange-red and soluble in benzene.

EXAMPLE 7

The procedure of example 1 was followed using as reaction mixture 0.32 g. of palladium sponge, 3 drops of distilled water and 40 ml. of glacial acetic acid. The reaction was carried out at a temperature of 127°-134° C. with a slow bubbling of nitric oxide (NO) and an occasional charge (3 times, total volume 130 ml.) of nitrogen dioxide ($NO_2$). After 50 minutes reaction time the addition of NO and $NO_2$ was stopped and argon was then bubbled through the mixture at 127°-134° C. for about one hour. The reaction solution was then cooled to ambient temperature and the palladium diacetate trimer crystallized out and was isolated by filtration. The dried crystals were obtained in 98% yield and were determined by infrared analysis to be the trimer of palladium diacetate. The product was found to be soluble in benzene and toluene.

EXAMPLE 8

The procedure of example 1 was followed with a reaction mixture composed of 0.3535 g. of palladium sponge and 45 ml. of glacial acetic acid. The reaction mixture was heated to 117°-132° C. for two hours and during this time it was maintained under an atmosphere of nitrogen dioxide ($NO_2$). At the very beginning of the reaction the mixture was flushed thoroughly with $NO_2$. After the two hour reaction period the temperature of the reaction mixture was held at 126°-129° C. for one hour and the residual $NO_2$ was removed from the mixture by flushing the mixture for an hour with argon. The reaction mixture was then cooled down to ambient temperature and the palladium diacetate precipitated out as orange-red crystals (93% yield) which were found by infrared analysis to be trimeric palladium diacetate.

EXAMPLE 9

The apparatus described in example 1 was used. The reaction mixture was composed of 0.82 g. of nitrosyl acetate (prepared from silver acetate and nitrosylchloride), 0.344 g. of palladium sponge and 40 ml. of glacial acetic acid. The resulting mixture was stirred at ambient temperature for three hours and then refluxed (110°-132° C.) for 2 hours and then maintained at this temperature for another hour while argon was bubbled through it. The reaction mixture was then cooled to ambient temperature and palladium diacetate precipitated out, was filtered and dried. The yield of product was quantitative.

EXAMPLE 10

The procedure of example 6 was repeated except that octanoic acid was used in place of acetic acid. The product was orange-red palladium dioctanoate which was obtained in about 80% yield.

EXAMPLE 11

The procedure of Example 6 was followed except that the reaction mixture was made up of 0.2 g. of palladium sponge, 42 g. of glacial acetic acid and 2 drops of distilled water. The reaction temperature was from 65°-70° C. and NO was bubbled slowly through the mixture under these conditions over a 20-25 minute period, during this time the mixture was periodically flushed with oxygen. All the palladium sponge dissolved during this time to give an orange-red solution which upon concentration afforded orange-red crystals of trimeric palladium acetate in 95% yield. The crystals were soluble in benzene and toluene and showed a sharp infrared band at 1600 cm$^{-1}$.

We claim:

1. A method for the preparation of a compound having the composition

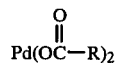

wherein R is a hydrocarbon or halogen substituted hydrocarbon group having from 1 to 10 carbon atoms comprising contacting palladium metal with a carboxylic acid having the formula RCOOH wherein R has the foregoing designation in the presence of a member selected from the group consisting of:

$HNO_2$,
nitric oxide and oxygen,
nitric oxide and nitrogen dioxide,
nitrogen dioxide, and
nitrosyl acetate at a temperature in the range of from 60° C. to 160° C. and recovering the product.

2. The method of claim 1 wherein the carboxylic acid is acetic acid.

3. The method of claim 1 wherein the carboxylic acid is trifluoro acetic acid.

4. The method of claim 1 wherein the carboxylic acid is octanoic acid.

5. The method of claim 2 wherein $HNO_2$ is employed.

6. The method of claim 2 wherein nitric oxide and oxygen are employed.

7. The method of claim 2 wherein nitric oxide and nitrogen dioxide are used.

8. The method of claim 2 wherein nitrogen dioxide is used.

9. The method of claim 2 wherein nitrosyl acetate is used.

10. The method of claim 4 wherein nitric oxide and oxygen are used.

* * * * *